(12) United States Patent
Bidan et al.

(10) Patent No.: US 8,389,696 B2
(45) Date of Patent: Mar. 5, 2013

(54) POLYMERIZABLE DIAZONIUM SALTS, PROCESS FOR THE PREPARATION THEREOF AND USES THEREOF

(75) Inventors: Gérard Bidan, Grenoble (FR); Bruno Jousselme, Massy (FR); Rémi De Bettignies, St Julien en Genevois (FR)

(73) Assignee: Commissariat a l'Energie Atomique, Paris (FR)

(*) Notice: Subject to any disclaimer, the term of this patent is extended or adjusted under 35 U.S.C. 154(b) by 311 days.

(21) Appl. No.: 12/750,424

(22) Filed: Mar. 30, 2010

(65) Prior Publication Data
US 2010/0184932 A1 Jul. 22, 2010

Related U.S. Application Data

(62) Division of application No. 11/782,218, filed on Jul. 24, 2007, now Pat. No. 7,812,139.

(30) Foreign Application Priority Data

Jul. 27, 2006 (FR) ...................................... 06 06906

(51) Int. Cl.
| | |
|---|---|
| C07C 245/00 | (2006.01) |
| H01L 31/00 | (2006.01) |
| H01L 29/15 | (2006.01) |
| H01L 31/0256 | (2006.01) |
| C25D 7/12 | (2006.01) |
| C25D 11/32 | (2006.01) |
| C25D 5/48 | (2006.01) |

(52) U.S. Cl. ........ 534/560; 136/263; 205/157; 205/220; 257/76; 257/E29.068

(58) Field of Classification Search .................... 136/263
See application file for complete search history.

(56) References Cited

U.S. PATENT DOCUMENTS

| | | | |
|---|---|---|---|
| 6,495,067 B1 | 12/2002 | Ono | |
| 2006/0005877 A1* | 1/2006 | Spivack et al. | 136/263 |
| 2006/0120954 A1* | 6/2006 | Brewer et al. | 423/657 |

OTHER PUBLICATIONS

Search Report for French Application NO. 0606906, filed Jul. 27, 2006.
Bottomley, F. et al.: "Electrophilic Behaviour of Nitrosyls"; J. Chem. Soc. Dalton Trans., 1982; pp. 1933-1937; XP009080489.
Isied, S. et al.,: "Rates of Substitution in Cis and Trans Ruthenium(II) Aquotetraamines"; Inorganic Chemistry; vol. 15, 1976; pp. 3070-3075; XP002424377.
Ware, D.C., Taube, H.: "Substitution-Induced N-N Coupling for Nitride Coordinated to Osmium(VI)"; Inorganic Chemistry; vol. 30, 1991; pp. 4605-4610; XP002424378. Magnuson, R.H., Taube, H.: "Synthesis and Properties of Osmium(II) and Osmium(III) Ammine Complexes of Aromatic Nitrogen Heterocyles"; J. Am. Chem. Soc.; 1975; pp. 5129-5136; XP002424379.

* cited by examiner

*Primary Examiner* — Peter F Godenschwager
*Assistant Examiner* — David Karst
(74) *Attorney, Agent, or Firm* — Alston & Bird LLP

(57) ABSTRACT

Polymerizable diazonium salts having redox properties and absorption in the visible range, a process for preparing them and uses thereof are disclosed. The salts have the general formula:

$$[X^{X+}L_nD_dE_m(N_2^+)_p][(B^-)_{p+x}]$$

in which:
X is chosen from transition metals, preferably X is chosen from ruthenium (Ru), osmium (Os), iron (Fe), cobalt (Co) and iridium (Ir),
x is an integer ranging from 1 to 5 inclusive,
L is a ligand chosen from pyridine, bipyridine, terpyridine, phenanthroline and phenylpyridine groups, and mixtures thereof,
n is an integer ranging from 1 to 5 inclusive,
D is a saturated or unsaturated, $C_1$-$C_5$ alkyl spacer compound,
d=0 or 1,
E is an aromatic or polyaromatic spacer compound that can contain one or more heteroatoms,
m is an integer ranging from 0 to 5 inclusive,
p is an integer, and
B is a counterion.

7 Claims, 4 Drawing Sheets

POLYMERIZABLE DIAZONIUM SALTS, PROCESS FOR THE PREPARATION THEREOF AND USES THEREOF

CROSS REFERENCE TO RELATED APPLICATIONS

This application is a divisional of U.S. patent application Ser. No. 11/782,218, filed Jul. 24, 2007, now U.S. Pat. No. 7,812,139 which claims priority to French Application No. 06 06906 filed Jul. 27, 2006, each of which is hereby incorporated herein in its entirety by reference.

FIELD AND BACKGROUND OF THE INVENTION

The invention relates to polymerizable diazonium salts which have redox properties and properties of absorption in the visible range at various wavelengths, to the process for preparing them and to uses thereof.

The functionalization, also referred to in the subsequent text as modification of electrically conductive or semiconductive surfaces with polymer films finds application in many fields, such as biology, electronics and optical components.

At the present time, there is an interest for at least two types of conductive or semiconductive surface modifications:
firstly, the modification of conductive or semiconductive surfaces with metal complexes, and
secondly, the functionalization of conductive or semiconductive surfaces using diazonium salts.

The modification of conductive or semiconductive surfaces with metal complexes results in hybrid devices and is of great value in the field of energy conversion, information storage, optics, or molecular electronics.

In fact, the properties and the behaviour of these hybrid electronic or optoelectronic devices are greatly influenced by the electron exchanges between the organic and inorganic part, and, consequently, by the nature of the chemical bonds between the organic molecules and the semiconductor and also by the amount and the nature of the grafted metal complex.

Thus, in the field of energy conversion, and more particularly in Grätzel photovoltaic cells, the semiconductive surface is modified with metal complexes.

In this case, the photoconversion is carried out by means of metal complexes which are bound to nanoparticles of $TiO_2$, $SnO_2$, ZnO or $ZrO_2$.

In these Grätzel cells, the ligands of the complexes comprise phosphonates, siloxanes, ethyl malonate, ether and/or cyanide functions which interact chemically with the surface of nanoparticles of $TiO_2$, $SnO_2$, ZnO or $ZrO_2$ which become grafted by means of bonds that are covalent or ionic in nature and give monolayers of complexes at the surface.

The metal complex in this type of device is the active component since it absorbs visible light and performs the charge separation.

In fact, photoexcitation of the metal complex (photosensitizer) which absorbs light produces the injection of one of its electrons into the conduction band of the semiconductor. The reduction of the oxidized complex leads to the formation of positive charges which are transported to the counter electrode by means of the conductive electrolyte ($I_3^-/I^-$). The oxidized photosensitizer is then reduced by the $I_3^-/I^-$ couple of the electrolyte so as to return to its initial state.

The energy which will be generated by this photovoltaic cell will therefore depend on the number of photons absorbed by the metal complex grafted at the surface of the nanoparticle.

However, the technique for grafting complexes in this type of device only makes it possible to produce monolayers of complex and therefore does not make it possible to absorb the entire intensity of the solar spectrum.

Furthermore, the use of the $I_3^-/I^-$ electrolyte, which is a liquid, poses a major problem. This is because it is difficult to obtain completely hermetic cells in which there is no leaking of the liquid electrolyte.

Moreover, in the context of information storage, the semiconductive surface of silicon is modified by the grafting of redox molecules, such as porphyrins or ferrocenes, onto this surface.

The organic compounds grafted onto these surfaces are the active compounds of the device since they are those which will be responsible for the memory effect through charge storage.

However, the methods of functionalization developed up until now are exclusively methods which involve chemical reactions such as the thermal activation of an alcohol, of a thiol, of a methyl halogenated derivative or of thiols that are protected with a surface of hydrogenated silicon or of halogenated silicon, the thermal hydrosyllilation of metal complexes comprising an alkene or alkyne function.

All these methods have various drawbacks, in particular the fact that the surface functionalization with these compounds is carried out at high temperatures, of the order of 200° C. to 400° C., conditions which are not compatible with all chemical compounds.

Furthermore, these reactions can also be extremely expensive in terms of product when they are carried out under solid conditions.

Similarly, with these various methods, the metal centre which has the redox properties is set apart by an arylmethylene bridge which distances it from the surface.

Finally, all these methods result only in the formation of monolayers and not polymers.

However, WO 2005/86826 A2 describes the formation of redox polymers on a silicon surface. The chemical method used consists in heating porphyrins comprising two alkyne functions to a temperature of between 200° C. and 400° C.

While said document indeed describes the formation of redox polymers on a conductive surface, this formation is again carried out by means of a reaction at high temperatures and cannot therefore be applied to all organic compounds.

Another means of functionalizing conductive or semiconductive surfaces is the electrochemical functionalization of these surfaces with diazonium salts.

Electrochemical functionalization with diazonium salts makes it possible to obtain polymers grafted to the surface, generally of silicon. It has been carried out using commercial diazonium salts which are 4-nitrophenyldiazonium tetrafluoroborate or 4-bromophenyldiazonium tetrafluoroborate.

The specific property of these diazonium salts is that they are grafted covalently with silicon and therefore form a strong interaction between molecules and substrate.

However, this method is limited since few diazonium salts exist because they are compounds that are unstable at ambient temperature and difficult to isolate.

Furthermore, the polymers formed and also the semiconductive surfaces formed cannot be used for information storage or energy conversion.

In fact, at the present time, no diazonium salts exist which could absorb visible light at various wavelengths and have redox or photoredox properties.

Another problem of this method, still due to the specificity of the diazonium salts used, is that the films deposited at the electrode by this method are thin. This is due to the deposition of nonconductive compounds on the surface, which do not make it possible to provide the charges in order to continue the electrochemical deposition, and therefore result in the deposition of an insulating film at the surface of the semiconductor.

This method is known in the literature for the functionalization of silicon surfaces, i.e. narrow-band semiconductive surfaces.

However, this method has never been described for the modification of wide-band semiconductors such as $TiO_2$, ZnO, SnO and $ZrO_2$.

SUMMARY OF THE INVENTION

The invention aims to solve the problems of the prior art by providing new graftable and polymerizable diazonium salts which have redox properties and properties of absorption in the visible range at various wavelengths.

These new diazonium salts permit the electrochemical polymerization of new metal complexes which become anchored on the conductive or semiconductive surface by means of a covalent bond and then polymerize so as to form a conductive film of controllable thickness on conductive or semiconductive surfaces, in particular the surface of n-type semiconductor nanowires.

These new diazonium salts also permit the synthesis of polymers with various layers of metal complexes and also the trapping of charges within the various layers of polymers for the production of information storage memory or for the transport of charges within the polymers so as to serve as a solid electrolyte, this being at ambient temperature.

Furthermore, these new diazonium salts can be grafted onto metal surfaces, in particular gold and platinum surfaces, and also onto carbon nanotubes of SWNT or MWNT type, nanoparticles, etc.

To this effect, a subject of the invention is polymerizable diazonium salts, characterized in that they have redox properties and properties of absorption in the visible range, and in that they have the following general formula (I):

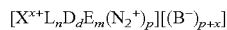

in which:

X is chosen from transition metals, preferably X is chosen from ruthenium (Ru), osmium (Os), iron (Fe), cobalt (Co) and iridium (Ir), x is an integer ranging from 1 to 5 inclusive, L is a ligand chosen from pyridine, bipyridine, terpyridine, phenanthroline and phenylpyridine groups, and mixtures thereof, n is an integer ranging from 1 to 5 inclusive, D is a saturated or unsaturated, $C_1$-$C_5$ alkyl spacer compound, d=0 or 1, E is an aromatic or polyaromatic spacer compound that can contain one or more heteroatoms, m is an integer ranging from 0 to 5 inclusive, p is an integer, and B is a counterion.

As can be seen from formula (I), the diazonium salts of the invention comprise a metal complex and one or more diazonium ions.

Conventionally, the metal complex consists of a metal centre, noted X in formula (I), to which are attached aromatic or polyaromatic ligands, noted L in formula (I). The metal complexes may be symmetrical, i.e. compounds having identical ligands, or nonsymmetrical, i.e. compounds having different ligands.

One or more diazonium functions are attached to the ligand of the metal complex either directly, or by means of a spacer, noted E in formula (I), or else by means of a first spacer, noted D in formula (I), which spacer D is then itself attached to the spacer E and to the ligand L.

By virtue of the presence of this or these diazonium(s), the salts of the invention make it possible to obtain films of polymer(s) on conductive or semiconductive surfaces.

The terms "conductive surface or semiconductive surface" is intended to mean an electrically conducting or semiconducting surface.

Preferably, the conductive surfaces are surfaces of stainless steel, iron, copper, nickel, cobalt, niobium, aluminium (in particular when it is freshly brushed), silver, gold, platinum, iridium or platinum-iridium alloy.

Preferably, the semiconductive surfaces are surfaces of doped or nondoped silicon, of titanium oxide ($TiO_2$), of tin oxide ($SnO_2$) of zinc oxide (ZnO) or of zirconia or zirconium oxide ($ZrO_2$). They can also be surfaces of SWNT or MWNT carbon nanotubes or nanoparticles.

However, more importantly, the polymer film obtained by virtue of the diazonium salts of the invention has reversible redox properties and properties of absorption of visible light at various wavelengths, due to the presence of the metal complex.

In formula (I), E is an aromatic or polyaromatic spacer compound that can contain one or more heteroatoms, such as a benzothiophene, benzofuran, indole, indoline, carbazole, dehydroquinoline, chromone, julodinine, thiadiazole, triazole, isoxasole, oxazole, thiazole, isothiazole, imidazole, pyrazole, thiazine, triazine, pyrazine, pyridazine, pyrimidine, diazepine, oxazepine, benzotriazole, benzoxazole, imidazole, benzimidazole, morpholine, piperidine, piperazine, azetidine, pyrrolidine or aziridine group.

As regards the counterion B, any counterion that makes it possible to obtain electroneutrality of the molecule can be used, such as a fosylate, a sulphonate, anionic polymers, such as polystyrenes, sulphonates, polyvinyl sulphonates and nafion.

Preferably, in formula (I), E is a phenyl, biphenyl, thiophene, bithiophene, furan, bifuran, pyridine, bipyridine, terpyridine, fluorene or fluorenone group, or mixtures thereof, and B is $PF_6$ or $BF_4$.

Examples of preferred diazonium salts according to the invention have one of the following general formulae I-2 to I-7:

Formula 1-2
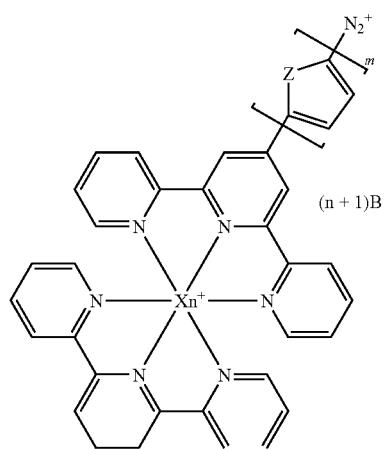
(n + 1)B
Formula I-5
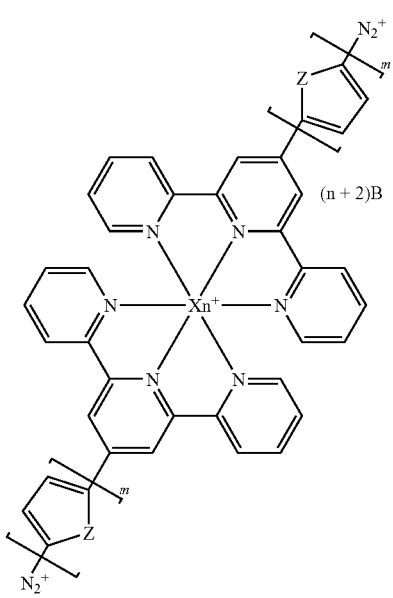
(n + 2)B
Formula 1-3
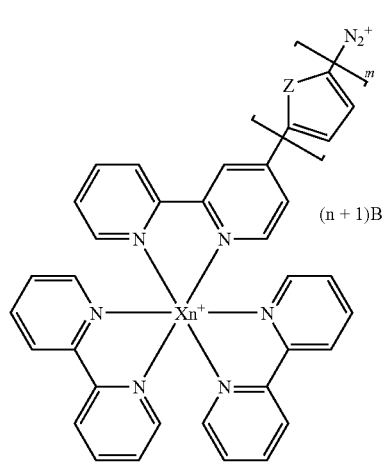
(n + 1)B
Formula I-4
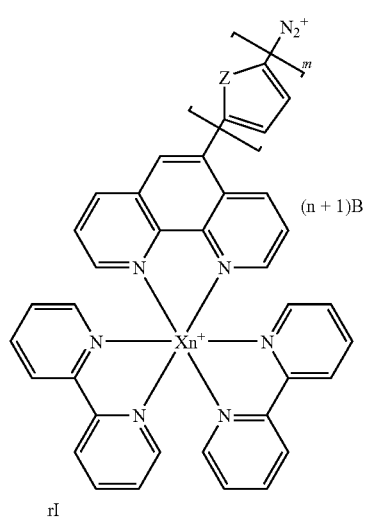
(n + 1)B
Formula I-6
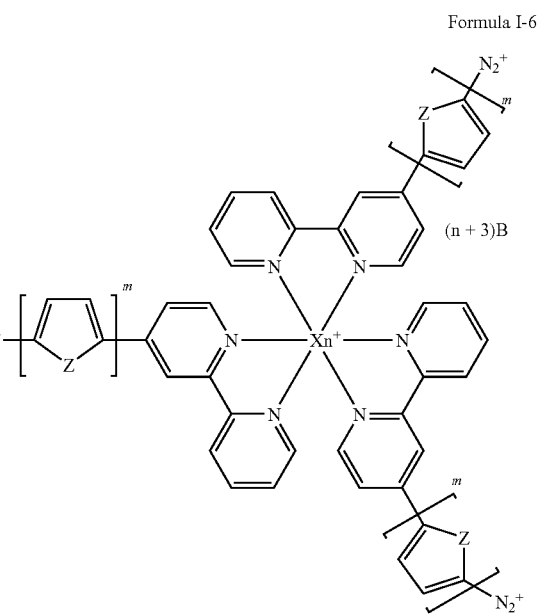
(n + 3)B Formula I-7

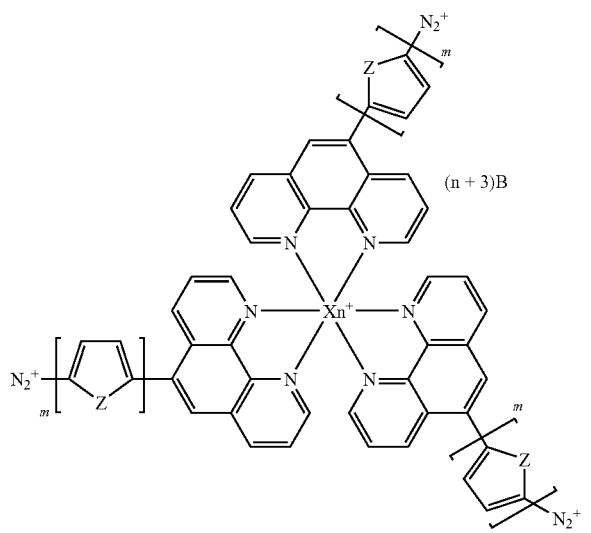

in which X is chosen from ruthenium (Ru), osmium (Os), iron (Fe), cobalt (Co) and iridium (Ir), Z is CH=CH, S, O, CH=N, N—H or N=N, m is an integer ranging from 0 to 5 inclusive, and B is preferably $BF_4$ or $PF_6$.

In formulae I-2 to I-7, the diazonium ion is linked to the metal complex by means of the spacer of formula

in which Z can be CH=CH, S, O, CH=N, N—H or N=N, and m is an integer ranging from 0 to 5 inclusive.

Other preferred diazonium salts according to the invention, in which the metal centre X can be ruthenium or osmium, have the following general formulae I-8 to I-12:

Formula I-8

Formula I-9

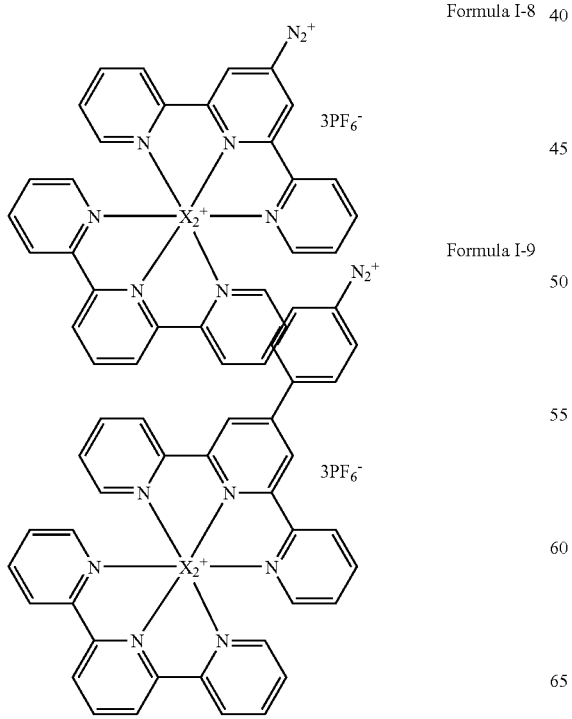

Formula I-10

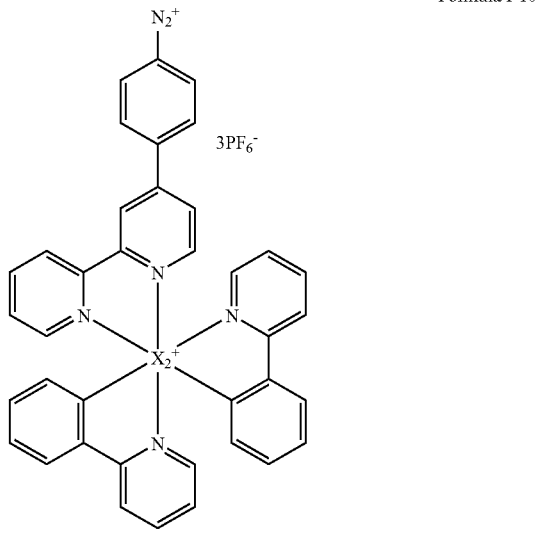

Formula I-11

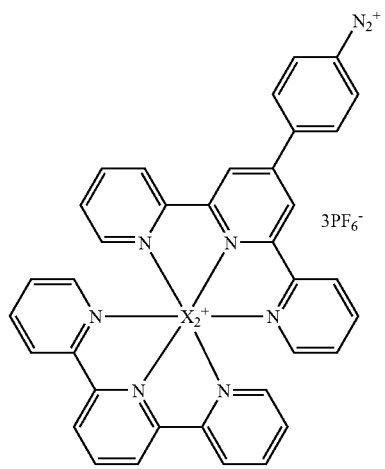

Formula I-12

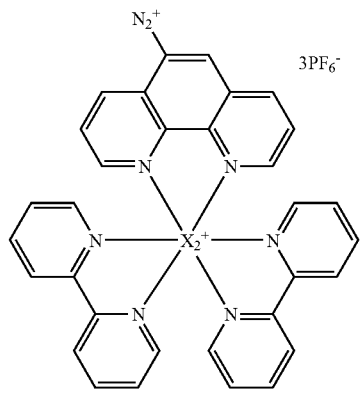

in which X is chosen from ruthenium (Ru) and osmium (Os).

In these diazonium salts, the counterion B is $PF_6$ and the diazonium ion is linked directly to the metal complex.

Even more preferred diazonium salts according to the invention have one of the following general formulae I-13 to I-14:

Formula I-13

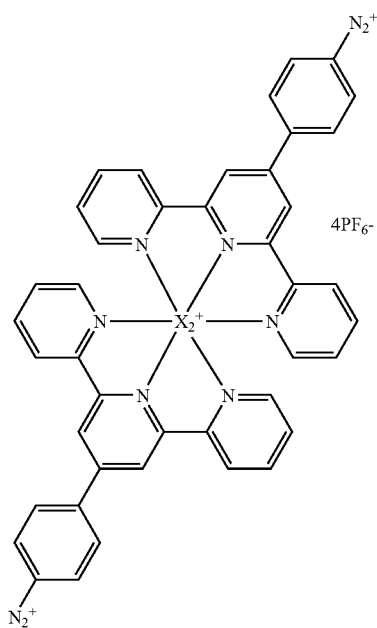

Formula I-14

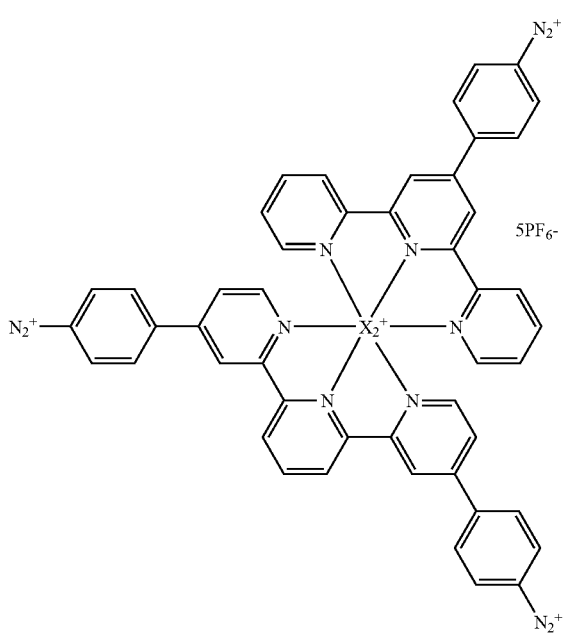

in which X is chosen from iron (Fe), ruthenium (Ru) and osmium (Os).

A particularly preferred diazonium salt according to the invention has the formula (I-15): [Ru (bipyridine)$_2$(bipyridine-phenyl-N$_2^+$)] [PF$_6$]$_3$.

Another particularly preferred diazonium salt according to the invention has the following formula (I-16): [Ir(phenylpyridine)$_2$(bipyridinephenyl-N$_2^+$)] [PF$_6$]$_2$ and the structural formula hereinafter:

Formula I-16

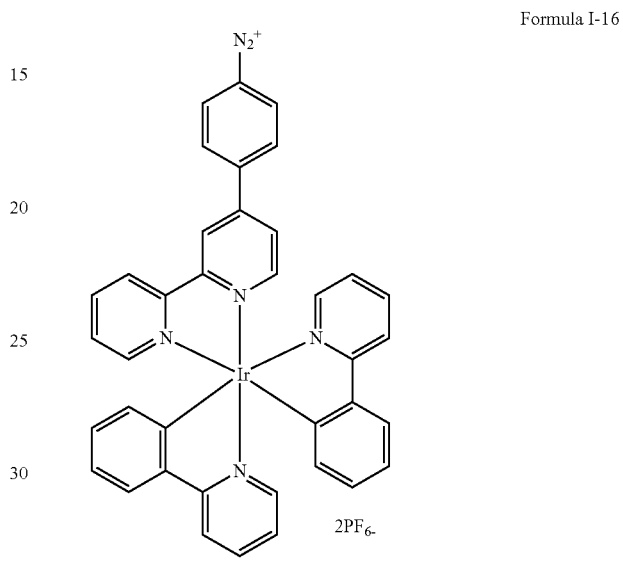

The general synthetic approach for obtaining the metal complex diazonium salts of the invention can be described in the following manner: firstly, the metal complexes are synthesized with at least one ligand according to a general method for synthesizing metal complexes such as that described in New. J. Chem, 1999, 53-61.

The ligands of the metal complex may be identical or different. However, they all have at least one aromatic amine function.

Then, the amine functions are converted to N$_2^+$ diazonium ions, using nitrosium tetrafluoroborate (NOBF$_4$) as described in J. Am. Chem. Soc. 2004, 126, 370-378.

This method was selected preferentially to the general method for obtaining diazonium salts, which is to use HBF$_4$/NaNO$_2$ and which gives a lower reaction yield.

Thus, a subject of the invention is also a process for synthesizing diazonium salts according to the invention, which comprises the steps of: (a) synthesizing the desired metal complex of formula XL$_n$ where all the ligands L have at least one aromatic amine function and may be identical or different, and (b) converting the amine functions to N$_2^+$ diazonium ions using NOBF$_4$.

The diazonium salts of the invention make it possible to obtain conductive or semiconductive surfaces coated with polymer films which have reversible redox properties and properties of absorption in the visible range at various wavelengths, according to the nature of the metal centre X.

The preparation of such surfaces is of great advantage in many fields, in particular for the manufacture of electronic components or optical devices, for the production of devices that can be used in the biomedical field or in biotechnologies, for anticorrosive protection, and also for all modifications of the surface properties of metals or of semiconductors.

Thus, in the context of energy conversion, and more particularly of Grätzel photovoltaic cells, where the photoconversion is carried out by means of metal complexes which are linked to nanoparticles of $TiO_2$, the diazonium salts of the invention can be used, firstly, to form a solid electrolyte, it being possible for this solid electrolyte to be composed of several layers of metal complexes, and, secondly, to form the active layer for photon absorption.

In fact, thanks to the diazonium salts of the invention, the polymer film formed is not insulating as in the prior art, and a second film of metal complex can be formed on the first polymer film formed.

The fact of having a multilayer solid electrolyte is a considerable advantage in Grätzel photovoltaic cells, first of all because it makes it possible to obtain completely hermetic cells in which there is no leaking of electrolyte. Indeed, in the prior art, the electrolyte was liquid.

Subsequently, the fact of being able to obtain several layers of different metal complexes grafted onto the $TiO_2$ surface allows the Grätzel cell to absorb the entire intensity of the solar spectrum, which is not the case in the prior art, where the metal complex grafting technique only made it possible to produce monolayers of complexes.

Furthermore, the possibility of producing films with various layers of organic compounds makes it possible to facilitate charge extraction.

Finally, thanks to the diazonium salts of the invention, it is possible to control the thickness of the films formed.

However, the diazonium salts of the invention are also of great advantage in information storage, i.e. for production of memories.

In this type of application, the organic compounds grafted onto the surface are the active compounds of the device since they are the ones which will be responsible for the memory effect through charge storage.

The diazonium salts of the invention which allow electrochemical grafting of such active compounds onto semiconductive surfaces, and in particular onto a silicon surface, make it possible to functionalize this surface under milder conditions with a wider choice of organic compounds, which makes it possible to explore many approaches for enhancing these memories.

Furthermore, the cost of this functionalization is reduced due to the small amount of compounds required for the functionalization.

In fact, the diazonium salts of the invention can be grafted onto the conductive or semiconductive surface by an electrochemical technique and not by a chemical technique as in the prior art, it being possible for the semiconductive surface to be a surface of a narrow-band semiconductor such as n-doped silicon, or a surface of a wide-band semiconductor such as ZnO.

The grafting method used is a rapid and direct method which is carried out in a single step.

Thanks to this method, it is possible to graft one or more layers of monomers at the surface of the semiconductor and to obtain polymers on the electrode.

The grafting of the metal complex diazonium salts of the invention is carried out at ambient temperature under potentiodynamic or static conditions. The semiconductive electrode is immersed in a solution composed of the degassed monomer in a solvent such as $CH_3CN$ or DMF, containing a background salt such as $LiClO_4$, $NR_4PF_6$ or $NR_4BF_4$, where R is a branched or unbranched $C_1$-$C_5$ alkyl chain, or ionic liquids such as the tetrafluoroborate salt of 1-butyl-3-methylimidazolium, the trifluoromethanesulphonate salt of 1-ethyl-3-methylimidazolium or the bromide salt of (4-pyridyl)pyridinium.

Reduction of the diazonium salt is obtained by negative polarization of the electrode, and this results in the formation of a radical. This radical will react with the hydrogen bonds of the support so as to form a covalent bond according to a radical process. This reaction is related to the number of electrons injected at the electrode in the solution. It will thus be possible to control the thickness of the film deposited, which can reach several hundred nanometres.

The production of polymer films with a thickness that can range from a few nanometres to several hundred nanometres is due to the specificity of diazonium salts of the invention.

In fact, the diazonium salts of the invention exhibit two waves of reversible reduction between $-1.6$ V and $-2$ V due to their redox properties. These redox properties make it possible to convey electrons at the surface of the film already deposited, and thus not only to propagate the polymerization so as to obtain the desired thickness, but also to obtain a conductive organic film at the surface of the electrode, which makes it possible to deposit, if desired, one or more additional films having an identical or different metal centre X.

The propagation of the polymerization takes place according to the following scheme 1:

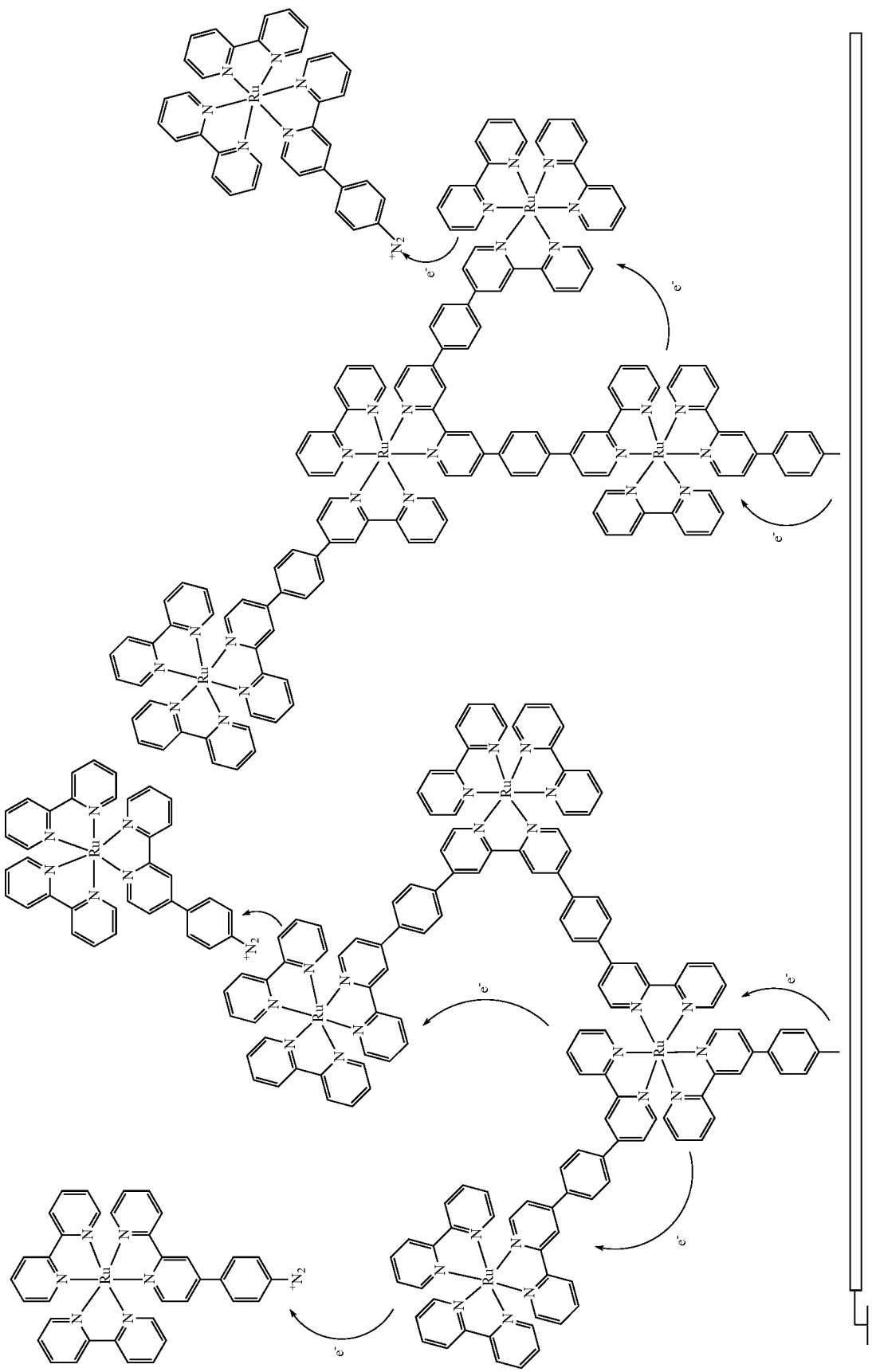
Scheme 1

This polymerization proceeds by grafting of the radicals onto the aromatic compounds, as seen from Scheme 1. The polymers obtained by this method are therefore entirely conjugated polymers.

This method has all the advantages of electrical targeting that the chemical method does not have, i.e. it makes it possible to control the amount of the compounds deposited, their position, etc. unlike the method of the prior art.

Furthermore, the diazonium salts of the invention make it possible to deposit layers of different metal complexes, having different redox properties, in order to increase charge storage and therefore memory performance levels.

In fact, thanks to the redox properties of the initial monomer, it is possible to graft several layers of polymers of different metal complexes.

For this, in a first step, a complex is deposited by electropolymerization onto the conductive or semiconductive surface. In a second step, a different monomer is used and electroplated onto the already formed layer. A bilayer is thus obtained at the electrode. In this manner, multilayers with different complexes, and which have different redox properties, can be produced.

The advantage of obtaining bilayers with complexes which have different redox properties is:
  to obtain rectifying surfaces, i.e., when two layers are sandwiched between two electrodes, the current will only be able to pass in one direction. This may make it possible to more readily extract the charges from a photovoltaic cell, and
  charge storage: since the current can pass only in one direction, it will be possible to store charges at the interface of the two layers in order to obtain a memory effect.

The functionalization of semiconductors is carried out in solutions with a low concentration of monomers (10 mmol to 0.1 mmol) and at ambient temperature, thereby making it possible to deposit compounds sensitive to high temperatures.

The polymers obtained thanks to the diazonium salts of the invention, as already stated, are polymers that are entirely conjugated due to the grafting of the radical A onto the aromatic compounds as shown in the above scheme. Given that the metal centres are close and separated by conjugated spacers, ion mobility within the layers is promoted, and the film formed can therefore serve as a solid electrolyte, in particular in Grätzel photovoltaic cells.

Finally, one of the major advantages of the diazonium salts of the invention is that they allow the electrofunctionalization of wide-band semiconductors such as $TiO_2$, $SnO_2$, ZnO and $ZrO_2$, which had never been carried out in the prior art.

Consequently, a subject of the invention is also, firstly, a process for forming a monolayer of polymer which has redox properties and properties of absorption in the visible range, on a conductive or semiconductive surface, which comprises a step of electrochemical grafting of a diazonium salt according to the invention and a step of polymerization of this diazonium salt, so as to obtain a film of polymer of the desired thickness, and, secondly, a process for forming multilayers of polymers which have redox properties and properties of absorption in the visible range, on a conductive or semiconductive surface, which comprises the steps of: (a) electrochemical grafting of a polymerizable diazonium salt according to the invention, onto said surface, (b) polymerization of this diazonium salt so as to form a first film of polymer of the desired thickness, (c) at least one step of grafting, onto the film obtained in step (a), of a polymerizable diazonium salt according to the invention, said diazonium salt being identical to or different from the diazonium salt used in step (a), and (d) polymerization of this diazonium salt, so as to form a second film, of the desired thickness.

In a first embodiment of these two processes, the semiconductive surface is a silicon surface.

In a second embodiment of these two processes, the semiconductive surface is the surface of a carbon nanotube.

In a third embodiment of these two processes, the semiconductive surface is the surface of a nanoparticle of titanium oxide ($TiO_2$), of tin oxide ($SnO_2$), of zinc oxide (ZnO) or of zircon ($ZrO_2$).

A subject of the invention is also a substrate which comprises at least one surface comprising at least one layer of polymer obtained from a polymerizable diazonium salt according to the invention.

A subject of the invention is also a device which comprises at least one substrate according to the invention.

Moreover, a subject of the invention is a photovoltaic cell, in particular of Grätzel type, which comprises at least one substrate according to the invention.

Furthermore, a subject of the invention is also a redox active cell for information storage which comprises at least one substrate according to the invention.

A subject of the invention is also a wide-band semiconductive device which comprises at least one substrate according to the invention.

More particularly, a subject of the invention is a Grätzel photovoltaic cell which comprises a solid electrolyte comprising at least one polymerizable diazonium salt according to the invention.

Finally, a subject of the invention is a solid conductive electrolyte which comprises at least one diazonium salt according to the invention.

BRIEF DESCRIPTION OF THE DRAWINGS

In addition to the above arrangements, the invention also comprises other arrangements, which will emerge from the description which follows, which refers to examples of implementation of the various subjects of the invention and also to the attached drawings, in which.

Figure 1:
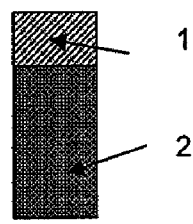
FIG. 1 represents an electrode onto the surface of which the diazonium salts of the invention can be covalently grafted.

It should be clearly understood, however, that these examples are given only by way of illustration of the subjects of the invention, on which they in no way constitute a limitation.

MORE DETAILED DESCRIPTION

Materials and Analytical Methods

In Examples 1 and 7 for the synthesis of the diazonium salts of the invention, the techniques used for characterizing the compounds obtained are nuclear magnetic resonance (NMR), infrared (IR) and UV (UV) spectrometric analysis, and mass spectrometry (MS).

The elemental chemical analysis was carried out by the analytical service of the CNRS [French National Centre for Scientific Research] of Vernaison (France).

The NMR spectra were recorded on a Bruker Avance AC 200 MHZ spectrometer (1H, 200.13 MHz and 13C, 50.32 MHz).

The chemical shifts are given with respect to TMS used as internal standard.

The IR spectra were recorded with a Perkin Elmer paragon 500 spectrometer.

The UV spectra were recorded with a Perkin Elmer Lambda 2 spectrometer.

The mass spectra were recorded with a thermofinnigan spectrometer equipped with an electrospray source.

All the reactants and the chemical products came from Aldrich or Acros.

Before it was used, the acetonitrile was distilled over $P_2O_5$ and the nitrosium tetrafluoroborate ($NOBF_4$) was purified by trituration in a 1:1 mixture of acetic anhydride and acetic acid.

Example 1

Synthesis of the Diazonium Salt of Formula I-15: [Ru(bipyridine)$_2$(bipyridinephenyl-$N_2^+$)] [$PF_6^-$]$_3$ The compound 4'-(4-aminophenyl)-2,2'-bipyridine required for the preparation of the diazonium salt of Formula I-15 was synthesized in several steps according to the literature.

Step 1: Synthesis of [Ru(bipyridine)$_2$(bipyridinephenyl-$N_2$)] [$PF_6$]$_2$

A solution of 4'-(4-aminophenyl)-2,2'-bipyridine (200 mg, 0.81 mmol) and of Ru(bipyridine)$_2$Cl$_2$·2H$_2$O (392 mg, 1 eq.) in ethanol (200 ml) is degassed and refluxed under an inert atmosphere (N$_2$) in the dark for 20 hours. The solution is then cooled and the residue is chromatographed on a silica gel (eluent: CH$_3$CH/H$_2$O/saturated aqueous KNO$_3$ solution, 40:4:1). The fractions containing the product are combined and an excess of NH$_4$ PF$_6$ is added. The acetonitrile is then evaporated off and the red solid obtained is filtered, and washed with water and ether ethyl to give [Ru(bipyridine)$_2$(bipyridinephenyl-NH$_2$)] [PF$_6$]$_2$ in the form of a red solid (540 mg, yield: 70%).

$^1$H NMR (DMSO-d$_6$): δ=9.10 (d, J=8.2 Hz, 1H); 8.96 (s, 1H), 8.86-8.82 (m, 4H); 8.25-8.10 (m, 5H); 7.88-7.70 (m, 8H); 7.60-7.48 (m, 6H); 6.70 (d, J=8.6 Hz, 2H); 5.85 (s, 2H).

$^{13}$C NMR (DMSO-d$_6$): δ=157.03; 156.66, 156.63; 156.60; 156.56; 156.48; 151.73; 151.22; 151.15; 151.09; 150.33; 148.56; 137.77; 128.42; 127.86; 127.67; 124.58; 124.44; 122.23; 120.80; 119.16; 118.09; 113.95.

IR v cm$^{-1}$; 3393, 3097, 1599, 1467, 1442, 1189, 1035, 828, 761.

UV/Vis (ACN) λ=288 nm (log ϵ=5.00), λ=352 nm (log ϵ=4.44), λ=457 nm (log ϵ=4.40).

MS-ESI: m/z [M-PF$_6$]+806.0, [M-2 PF$_6$-]2+330.6. Elemental analysis calculated as a percentage for C$_{36}$H$_{29}$N$_7$RuP$_2$F$_{12}$: C, 45.42; H, 3.07; N, 10.31. Found: C, 45.71; H, 3.23; N, 10.37.

Step 2: [Ru (bipyridine)$_2$(bipyridinephenyl-$N_2^+$)] [PF$_6$]$_3$

Under an inert atmosphere, a solution of compound obtained in step 1 [Ru(bipyridine)$_2$(bipyridinephenyl-NH$_2$)] [PF$_6$]$_2$ (250 mg, 0.26 mmol) in 2 ml of distilled acetonitrile is degassed and added to a solution of NOBF$_4$ (37 mg, 1.2 eq.) in 2 ml of distilled acetonitrile under argon at −40° C. The mixture is stirred at this temperature for 30 minutes and 50 ml of ethyl ether are added to the mixture. The precipitate formed is filtered off, and washed several times with ethyl ether. The compound obtained is a brown solid (280 mg, yield: 97%).

$^1$H NMR (DMSO-d$_6$): δ=9.27 (s, 1H), 9.10 (d, J=8.0 Hz, 1H); 8.90-8.80 (m, 6H); 8.54 (d, J=8.6 Hz, 2H); 8.30-8.10 (m, 5H); 7.98-7.85 (m, 2H); 7.85-7.70 (m, 5H); 7.62-7.45 (m, 5H).

IR v cm$^{-1}$; 3114, 2275 (N≡N), 1587, 1452, 1394, 1189, 1035, 837, 764.

UV/Vis (ACN) λ=287 nm (log ϵ=4.87), λ=455 nm (log ϵ=4.14).

Example 2

Electrografting of the Diazonium Salt Obtained in Example 1 onto a Narrow-band (N-doped Silicon) Semiconductor Electrode A conventional three-electrode electrochemical assembly: working electrode, reference electrode and counter electrode, is used.

FIG. 1 represents the electrode onto the surface of which the diazonium salt obtained in Example 1 will be covalently grafted. This electrode has a chromium-gold contact block, noted 1 in FIG. 1, which ensures good conduction with the n-doped silicon, noted 2 in FIG. 1, and makes it possible to take a point of contact in order to perform the electrografting.

Before the electrografting, the silicon electrodes are soaked for one minute in a 1% solution of hydrofluoric acid (HF), and then in water, and finally in isopropanol in order to remove the layer of native oxide and to obtain a hydrogenated silicon surface.

The working electrode is then immersed in a degassed acetonitrile solution comprising an electrolyte (LiClO$_4$, NBu$_4$ PF$_6$ (0.1 M)) and the diazonium salt obtained in Example 1. The electrografting was subsequently carried out under potentiodynamic or potentiostatic conditions, at ambient temperature.

Figure 2:
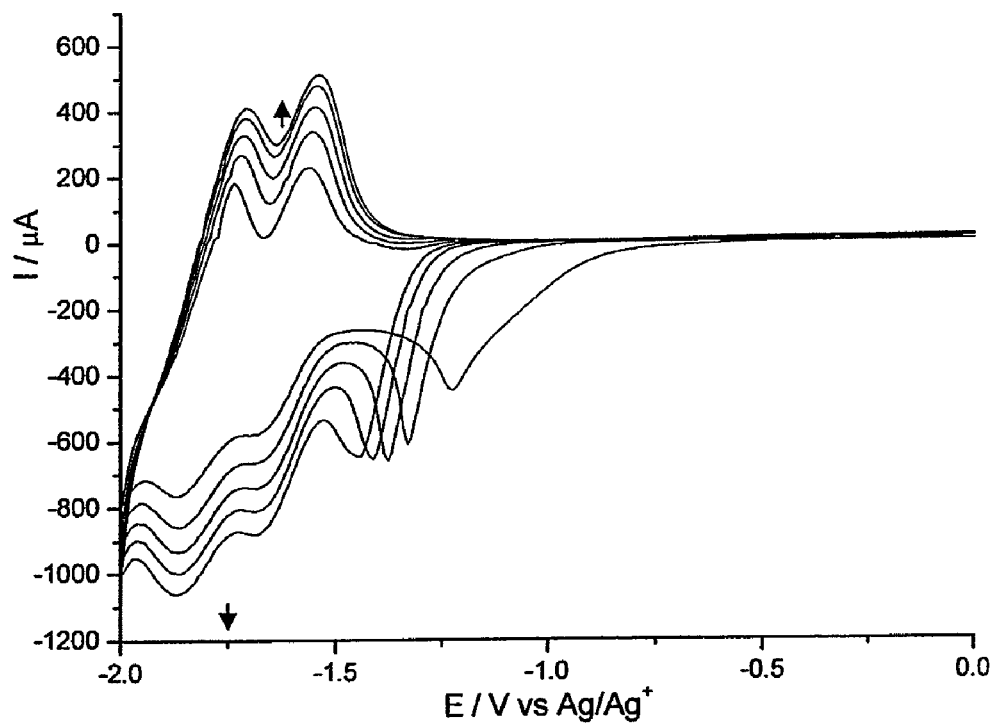
FIG. 2 represents the cyclic voltammetry curve obtained during the electrografting of the diazonium salts obtained in Example 1 onto the electrode represented in FIG. 1.

FIG. 2 represents the cyclic voltammetry curve obtained during the electrografting of the diazonium salt obtained in Example 1 onto a highly n-doped silicon electrode (8×10$^{-3}$/ 2×10$^{-2}$ Ω·cm) when dynamic scanning of the potential is performed for the 5 cycles between 0 and −2 V as a function of Ag/Ag$^+$.

As is seen in FIG. 2, during the first scan, the voltamogram shows an irreversible wave around −1.15 V, which corresponds to the reduction of the diazonium salt to a radical which reacts with the hydrogenated silicon surface so as to form covalent bonds, and two reversible waves of reduction around −1.5 V and −1.75 V. These two reversible waves of reduction are linked to the reduction of the bipyridine, terpyridine or phenanthroline ligands.

The increase in current intensity of the waves of reduction of the ligands of the complex when cycling between 0 and −2 V is characteristic of a modification of the surface of the electrode.

Figure 3:
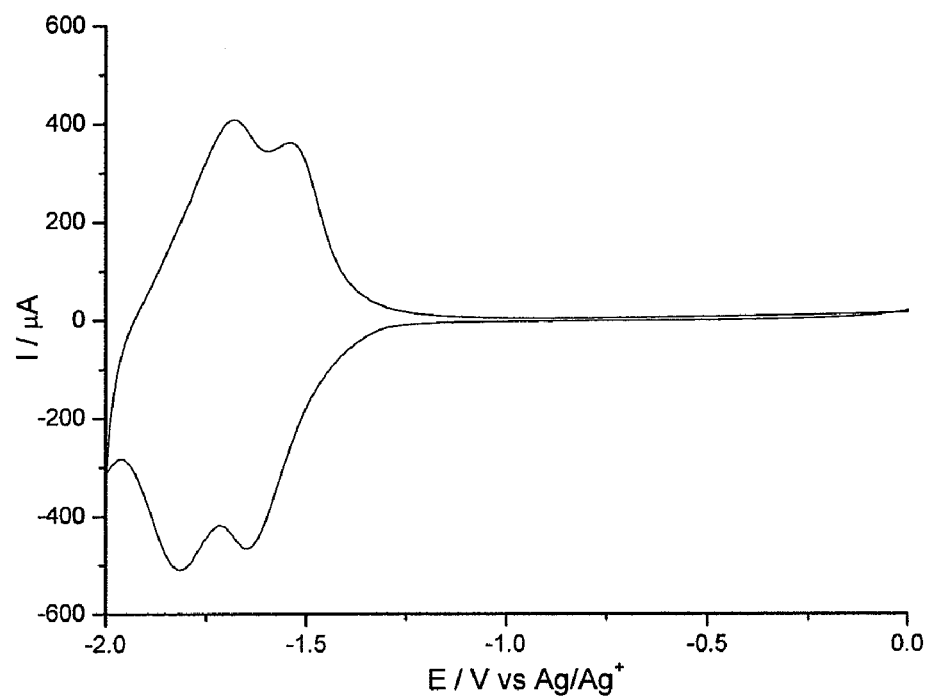
FIG. 3 represents the cyclic voltammetry (CV) curve for the electrode of FIG. 1, the surface of which has been modified by the formation of a polymer film obtained from a diazonium salt according to the invention and put into operation in an analytical medium free of diazonium salt according to the invention.

FIG. 3 represents the cyclic voltammetry curve produced on the modified electrode, i.e. with a film of the polymer obtained from the diazonium salt of Example 1. In this case, the analytical medium was free of diazonium salt according to the invention.

This curve clearly shows the deposition of ruthenium complex at the surface of the silicon electrode.

In fact, after washing of the electrode with solvents in which the initial complex is soluble, the voltammetry curves show the two reversible waves of reduction characteristic of the complex with potentials identical to the initial complex.

This shows that the films of polymer grafted onto the silicon electrode have redox properties which make it possible not only to transport electrons to the surface of the film already deposited so as to propagate the polymerization and thus to obtain films of polymers with a thickness that can range up to a few hundred nanometers, but also to obtain a conductive organic film at the surface of the electrode, which makes it possible to deposit, if desired, a second layer of polymer of a different metal complex on the film already formed.

Example 3

Electrografting of the Diazonium Salt Obtained in Example 1 onto a Wide-Band Semiconductor (Zno)

The procedure was carried out as in Example 2 above, but using ZnO electrodes.

The cyclic voltammetry curves obtained are identical to those obtained in Example 2.

This example shows that it is possible, by virtue of the diazonium salts of the invention, to electrofunctionalize wide-band semiconductors, which had never been done in the prior art.

Example 4

Capture of Charges in the Polymers Obtained from the Diazonium Salt of Example 1

Figure 4:
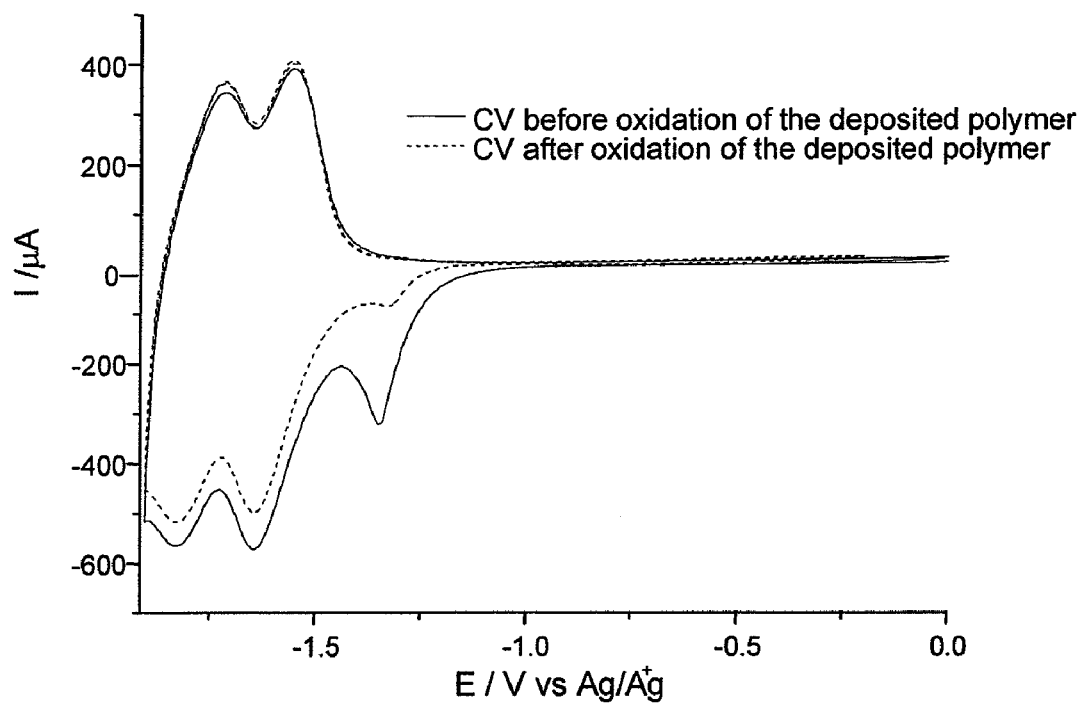
FIG. 4 represents the cyclic voltammetry (CV) curve for the modified electrode shown in FIG. 3, before and after oxidation of the metal centre.

FIG. 4 demonstrates the capture of charges in the electrografted polymer obtained from the diazonium salt of Example 1 when the metal centre of the complex grafted at the electrode was oxidized, regardless of whether this electrode is an n-doped silicon electrode or a ZnO electrode.

In FIG. 4, the solid-line voltamogram corresponds to the response of a film obtained by formation of the diazonium salt obtained in Example 1 in the potentiostatic mode, after oxidation of the metal centre, and the dashed-line voltamogram corresponds to the response for a film obtained from the diazonium salt obtained in Example 1 in the potentiostatic mode, before oxidation of the metal centre.

The film shows the two reversible waves of ligand reduction. When the electrode is then brought to a potential of 1.2 V as a function of Ag/Ag$^+$, the electrochemical response of the polymer deposited at the electrode changes and shows an additional irreversible wave around −1.3 V. This corresponds to the reduction of the charges captured during the oxidation of the metal centre.

This demonstrates that charges became stored in this type of polymer and that, consequently, this type of polymer can be used in information storage.

Example 5

Figure 5:
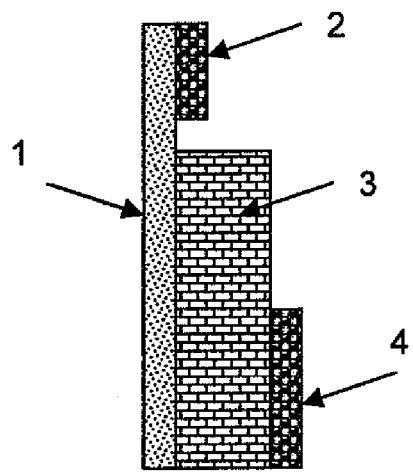
FIG. 5 represents a view from the side of a device consisting of an n-doped silicon electrode with its chromium-gold contact at the surface of which has been grafted the polymer obtained from the diazonium salts of the invention under potentiodynamic conditions.

Use of the Polymer Obtained from the Diazonium Salt Obtained in Example 1, as Solid Electrolyte FIG. 5 represents a view from the side of a device consisting of an n-doped silicon electrode (14/22 Ω·cm), noted 1 in FIG. 5, with its chromium-gold contact, noted 2 in FIG. 5, on which has been formed the polymer obtained from the diazonium salt synthesized in Example 1, noted 3 in FIG. 5, under potentiodynamic conditions (thickness of 40 to 100 nm).

A metal electrode made of gold, noted 4 in FIG. 5, was then deposited directly onto the film 3 by vacuum evaporation.

Irradiation with white light (power of 100 Mw/cm$^2$) causes a current which is due to the absorption of the light by the silicon semiconductor.

Figure 6:
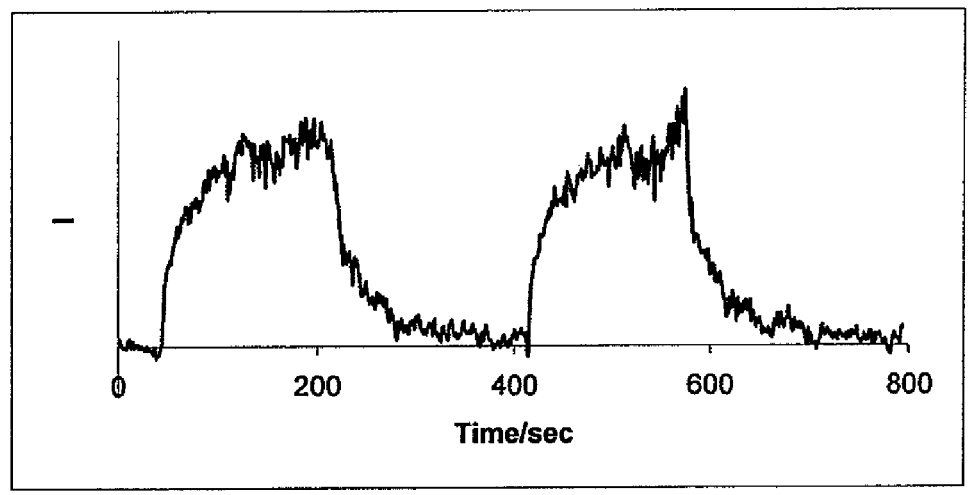
FIG. 6 represents the photocurrent caused by the irradiation, with white light, of the device represented in FIG. 5.

FIG. 6 represents the photocurrent thus induced.

The absorption of light by the silicon semiconductor generates charges inside the semiconductor, which can be extracted by means of the transport of gaps in the redox polymer previously formed.

In this example, the polymer serves as a solid electrolyte and makes it possible to prevent the photoanodic decomposition generally obtained when a liquid electrolyte is used.

Example 6

Formation of Various Layers of Metal Complexes on a Silicon Surface

Thanks to the specificity of the diazonium salts of the invention, it is possible to graft several layers of metal complexes onto an electrode.

Figure 7:
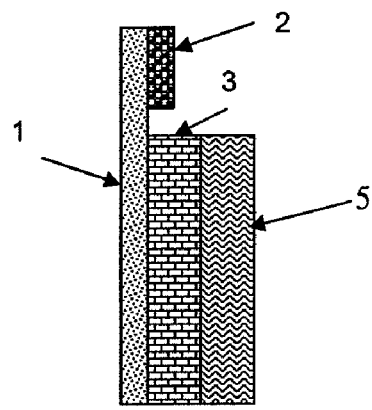
FIG. 7 represents a view from the side of a device consisting of an n-doped silicon electrode with its chromium-gold contact on which a first film of a polymer obtained from a diazonium salt of the invention, comprising a ruthenium metal complex, has been formed, and then a second film of a polymer obtained from a diazonium salt of the invention has been formed, on the first film.

FIG. 7 shows a view from the side of a device consisting of an n-doped silicon electrode, noted 1 in FIG. 7, with its chromium-gold metal contact, noted 2 in FIG. 7, on which has been formed a first layer of the diazonium salt obtained in Example 1, noted 3 in FIG. 7.

It is then possible to recommence the electroplating of another metal complex onto this layer 3, so as to obtain a layer, noted 5 in FIG. 7.

It is thus possible to manufacture electrodes on which there are several layers of metal complexes. These layers are then capable of storing charges for the production of memories.

Example 7

Synthesis of the Diazonium Salt of Formula I-16: [Ir(phenylpyridine)$_2$(bipyridinephenyl-N$_2^+$] [PF$_6$]$_2$ Step 1: Synthesis of [Ir(phenylpyridine) (bipyridinephenyl-N$_2^+$)] [PF$_6$]$_2$ A solution of 4'-(4-aminophenyl)-2,2'-bipyridine (100 mg, 0.4 mmol) and of tetrakis(2-phenylpyridine-C$_{2-}$, N') (μ-dichloro)diiridium (215 mg, 0.5 eq.) (metal precursor which was synthesized according to the procedure described by Watt et al., J. Am. Chem. Soc. 1984, 106, 6647) in a 1/1 methanol/dichloromethane mixture (30 ml) is refluxed under an inert atmosphere (Ar) for 8 hours. After a return to ambient temperature, 2 ml of a saturated KPF$_6$ solution are added and the solvents are then evaporated off in a rotary evaporator. The yellow solid obtained is then tritiated in water and then filtered and washed several times with water and then with ethyl ether. The solid is then dissolved in acetonitrile and chromatographed on a silica gel (eluent: $CH_3CN/H_2O$/saturated aqueous $KNO_3$ solution 18:2:1). The fractions containing the product are combined and an excess of $NH_4PF_6$ is added. The acetonitrile is then evaporated off and the yellow solid obtained is filtered, and washed with water and with ethyl ether, to give [Ir(phenylpyridine)$_2$(bipyridinephenyl-$NH_2$)][$PF_6$] in the form of a yellow powder (220 mg, 62%).

$^1$H NMR (acetone-d$_6$): δ=9.05 (d, J=8.3 Hz, 1H); 8.95 (d, J=1.9 Hz, 1H); 8.36-8.18 (m, 3H); 8.08 (d, J=5.5 Hz, 1H); 8.00-7.73 (m, 10H); 7.67 (t, J=6.3 Hz, 1H); 7.16 (m, 2H); 7.03 (t, J=7.6 Hz, 2H); 6.90 (d, J=7.3 Hz, 2H); 6.82 (d, J=8.6 Hz, 2H); 6.38 (d, J=7.1 Hz, 2H); 5.44 (s, 2H).

IR δ cm$^{-1}$; 3393, 3097, 1599,

UV/Vis (ACN) λ=377 nm, λ=337 nm.

MS-ESI: m/z [M−PF$_6$] 748.

Elemental analysis calculated as a percentage for $C_{38}H_{29}N_5IrPF_6$:

C, 51.12; H, 3.27; N, 7.84. Found: C, 50.96; H, 3.17; N, 7.58.

Step 2: Synthesis of the Diazonium Salt [Ir(phenylpyridine)$_2$(bipyridinephenyl-$NH_2$)] [$PF_6$]

In an inert atmosphere, a solution of [Ir(phenylpyridine)$_2$(bipyridinephenyl-$N_2^+$)] [$PF_6$] (100 mg; 0.11 mmol) in 2 ml of distilled acetonitrile is degassed and added to a solution of $NOBF_4$ (16 mg, 1.2 eq.) in 2 ml of distilled acetonitrile under argon at −40° C. The mixture is stirred at this temperature for 30 minutes and 50 ml of ethyl ether are added. The precipitate formed is filtered off, and washed several times with ethyl ether. The compound obtained is a yellowy brown solid (107 mg, 98%).

$^1$H NMR (DMSO-d6): δ=9.31 (s, 1H); 9.15 (d, J=8.4 Hz, 1H); 8.46 (d, J=8.6 Hz, 2H); 8.54 (d, J=8.6 Hz, 2H); 8.45-8.22 (m, 3H); 8.17 (d, J=4.9 Hz, 1H); 8.07-7.86 (m, 6H); 7.80-7.60 (m, 3H); 7.25-6.85 (m, 6H); 6.21 (t, J=6.0 Hz, 2H).

IR σcm$^{-1}$: 2276 (N≡N).

Step 3: Grafting and Electrochemical Polymerization of the Diazonium Salt [[Ir(phenylpyridine)$_2$(bipyridinephenyl-$NH_2$)] [$PF_6$] on a Platinum Electrode The assembly used is identical to that used in Examples 2 and 3 for the electroplating of the ruthenium complex. In this example, the complex is grafted and polymerized on a metal surface which is platinum.

Figure 8:
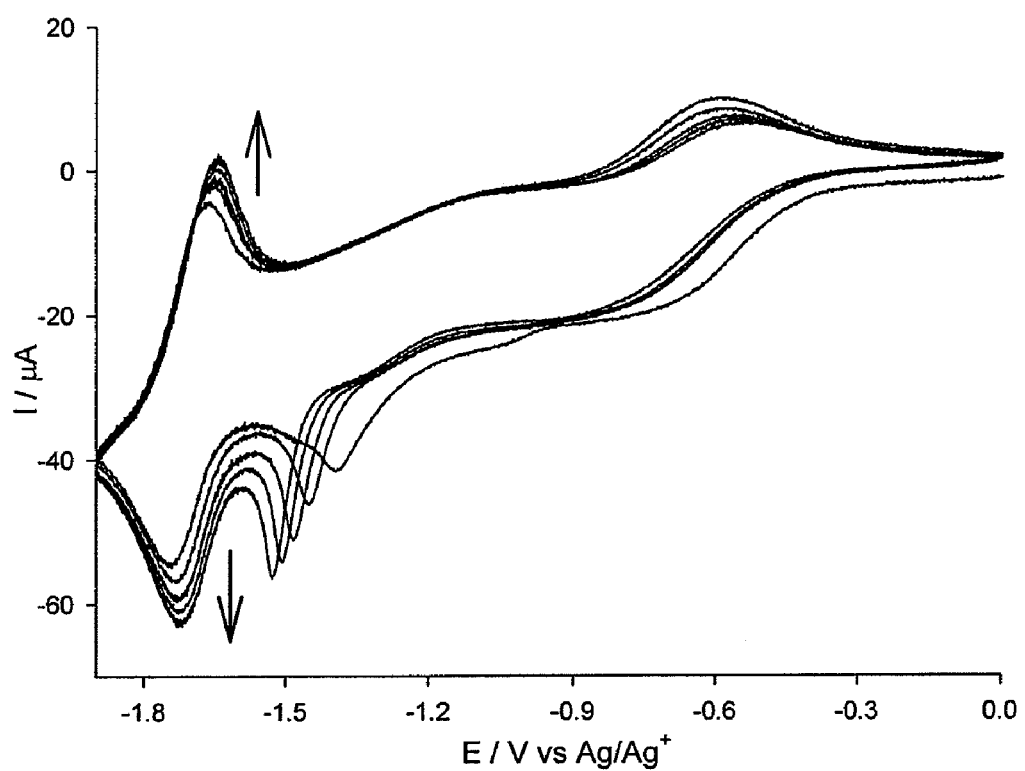
FIG. 8 represents the cyclic voltammetry curve obtained during the electrografting of the diazonium salts obtained in Example 7 onto the electrode represented in FIG. 1.

FIG. 8 represents the voltammetry curve obtained during the grafting of the diazonium salt of the iridium complex obtained above onto a platinum electrode when dynamic scanning of the potential is performed for 5 cycles between 0 and −1.9 V as a function of Ag/Ag$^+$. FIG. 8 shows an irreversible wave around −1.39 V, which corresponds to the formation of a cation radical of the diazonium salt, and a reversible reduction wave at −1.7 V, corresponding to the reduction of the complex. The increase in current intensity during the cycling between 0 and −1.9 V clearly shows the formation of a deposit on the iridium complex on the surface of the electrode.

Although the above examples have shown the advantages of the diazonium salts of the invention for the electrochemical deposition of various layers of metal complexes onto a silicon, zinc oxide or platinum surface, the invention is in no way limited to the electrofunctionalization of silicon, ZnO or platinum surfaces.

In fact, the electrofunctionalization of $TiO_2$, $SnO_2$ or $ZrO_2$ surfaces or surfaces of SWNT or MWNT carbon nanotubes, of nanoparticles, and of any conductive surfaces such as gold surfaces, iridium surfaces, iron surfaces, aluminium surfaces, etc., can be carried out in the same way.

Similarly, although the invention has been described in the examples above as having applications in the fields of energy conversion and information storage, the diazonium salts of the invention may make it possible to prepare other devices in which the electrofunctionalization of a conductive or semiconductive surface is advantageous.

In addition, although the examples make reference to the formation of biolayers of different metal compounds on a substrate, it will be clearly apparent to those skilled in the art that as many different or identical layers may be deposited on at least one conductive or semiconductive surface of a substrate.

The invention claimed:

1. A substrate, having at least one surface comprising at least one layer of polymer obtained from a polymerizable diazonium salt having the following formula (I):

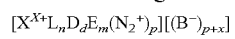   Formula I in which:
X is a transition metal selected from the group consisting of ruthenium (Ru), osmium (Os), iron (Fe), cobalt (Co) and iridium (Ir),
x is an integer ranging from 1 to 5 inclusive,
L is a ligand chosen from pyridine, bipyridine, terpyridine, phenanthroline and phenylpyridine groups, and mixtures thereof,
n is an integer ranging from 1 to 5 inclusive,
D is a saturated or unsaturated, $C_1$-$C_5$ alkyl spacer compound
d=0 or 1,
E is an aromatic or polyaromatic spacer compound that can contain one or more heteroatoms,
m is an integer ranging from 0 to 5 inclusive,
p is an integer >0, and
B is a counterion.

2. A Device, characterized in that it comprises at least one substrate according to claim 1.

3. A Photovoltaic cell of Grätzel type, characterized in that it comprises at least one substrate according to claim 1.

4. A Redox active cell for information storage, characterized in that it comprises at least one substrate according to claim 1.

5. A Wide-band semiconductive device, characterized in that it comprises at least one substrate according to claim 1.

6. A substrate having a polymer layer covalently bonded thereto, the polymer layer being obtained from a polymerizable diazonium salt having the following formula (I):

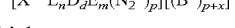   Formula I in which:
X is a transition metal,
x is an integer ranging from 1 to 5 inclusive,
L is a ligand chosen from pyridine, bipyridine, terpyridine, phenanthroline and phenylpyridine groups, and mixtures thereof,
n is an integer ranging from 1 to 5 inclusive,
D is a saturated or unsaturated, $C_1$-$C_5$ alkyl spacer compound
d =0 or 1,
E is an aromatic or polyaromatic spacer compound that can contain one or more heteroatoms,
m is an integer ranging from 0 to 5 inclusive,
p is an integer >0, and
B is a counterion.

7. The substrate according to claim 6, wherein X is selected from the group consisting of ruthenium (Ru), osmium (Os), iron (Fe), cobalt (Co) and iridium (Ir).

* * * * *

UNITED STATES PATENT AND TRADEMARK OFFICE
CERTIFICATE OF CORRECTION

PATENT NO. : 8,389,696 B2
APPLICATION NO. : 12/750424
DATED : March 5, 2013
INVENTOR(S) : Bidan et al.

It is certified that error appears in the above-identified patent and that said Letters Patent is hereby corrected as shown below:

In the Specifications:

Column 5,
Lines 1-20, Formula 1-2 should appear as follows:

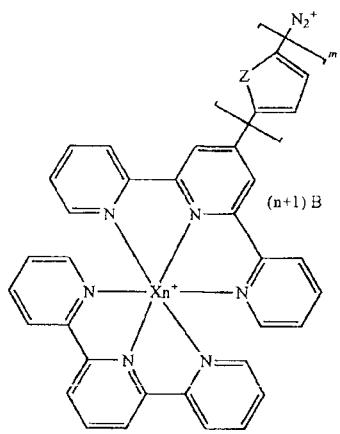

Formula 1-2

Column 7,
Lines 40-67, Formula I-8 and Formula I-9 should be separated to appear as follows:

Formula I-8

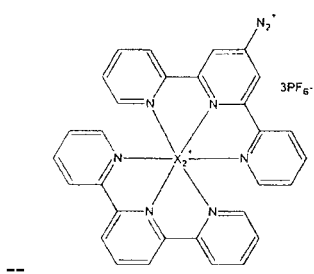

--

Signed and Sealed this
Fourth Day of June, 2013

Teresa Stanek Rea
*Acting Director of the United States Patent and Trademark Office*

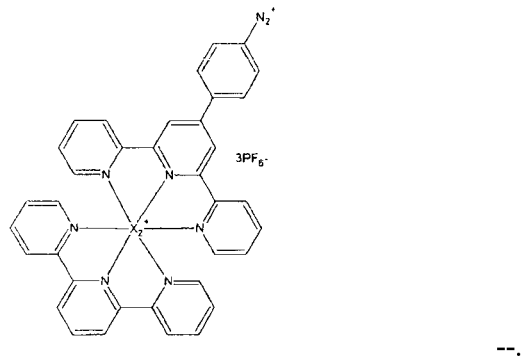

Formula I-9

--.

Column 20,
Line 54, "[Ir(phenylpyridine)$_2$(bipyridinephenyl-N$_2^+$][PF$_6$]$_2$" should read --[Ir(phenylpyridine)$_2$(bipyridinephenyl-N$_2^+$)][PF$_6$]$_2$--;
Line 56, "[Ir(phenylpyridine) (bipyridinephenyl-N$_2^+$)][PF$_6$]$_2$" should read --[Ir(phenylpyridine)$_2$(bipyridinephenyl-N$_2^+$)][PF$_6$]$_2$--;
Line 67, "tritiated" should read --tritated--.

Column 21,
Line 17, "MS-ESI: m/z [M − PF$_6$] 748." should read --MS-ESI: m/z [M − PF$_6$]$^+$ 748.--.

In the Claims:

Column 22,
Lines 32 and 59, "p is an integer >0,and" should read --p is an integer > 0, and--.